United States Patent [19]
Bacich et al.

[11] Patent Number: 5,749,889
[45] Date of Patent: May 12, 1998

[54] METHOD AND APPARATUS FOR PERFORMING BIOPSY

[75] Inventors: Steven R. Bacich, Laguna Niguel; John P. Greelis, Aliso Viejo; Hien Nguyen, Santa Ana; Tuoc Nguyen, Westminster, all of Calif.

[73] Assignee: Imagyn Medical, Inc., Laguna Niguel, Calif.

[21] Appl. No.: 600,608

[22] Filed: Feb. 13, 1996

[51] Int. Cl.$^6$ .............. A61M 29/00; A61M 5/178; A61M 5/32; A61M 5/00
[52] U.S. Cl. .............. 606/198; 600/104; 600/153; 604/104; 604/158; 604/162; 604/264
[58] Field of Search .............. 606/198; 604/103, 604/104, 164, 198, 264, 158, 159, 162, 163, 171, 280, 281; 600/104, 153, 156

[56] References Cited

U.S. PATENT DOCUMENTS

| | | |
|---|---|---|
| 1,150,214 | 8/1915 | London . |
| 2,548,602 | 4/1951 | Greenburg . |
| 3,656,485 | 4/1972 | Robertson . |
| 3,789,852 | 2/1974 | Kim . |
| 4,141,364 | 2/1979 | Schultze . |
| 4,211,234 | 7/1980 | Fisher . |
| 4,406,656 | 9/1983 | Hattler ert al. . |
| 4,503,843 | 3/1985 | Boebel . |
| 4,601,713 | 7/1986 | Fuqua . |
| 4,610,242 | 9/1986 | Santangelo et al. . |
| 4,646,722 | 3/1987 | Silverstein et al. . |
| 4,688,554 | 8/1987 | Habib . |
| 4,718,406 | 1/1988 | Bregman et al. . |
| 4,721,097 | 1/1988 | D'Amelio . |
| 4,738,666 | 4/1988 | Fuqua . |
| 4,784,117 | 11/1988 | Miyazaki . |
| 4,798,193 | 1/1989 | Giesy et al. . |
| 4,800,870 | 1/1989 | Reid, Jr. . |
| 4,928,669 | 5/1990 | Sullivan . |
| 5,025,778 | 6/1991 | Silverstein et al. . |
| 5,106,368 | 4/1992 | Uldall et al. . |
| 5,201,908 | 4/1993 | Jones . |
| 5,213,092 | 5/1993 | Uram . |
| 5,217,001 | 6/1993 | Nakao et al. . |
| 5,232,446 | 8/1993 | Arney . |
| 5,318,588 | 6/1994 | Horzewski et al. . |
| 5,320,091 | 6/1994 | Grossi et al. . |
| 5,334,167 | 8/1994 | Cocanower . |
| 5,374,247 | 12/1994 | Lowery et al. . |
| 5,378,230 | 1/1995 | Mahurkar . |
| 5,386,817 | 2/1995 | Jones . |
| 5,413,560 | 5/1995 | Solar . |
| 5,503,616 | 4/1996 | Jones . |
| 5,573,508 | 11/1996 | Thornton . |

FOREIGN PATENT DOCUMENTS

| | | |
|---|---|---|
| B-85530/91 | 5/1992 | Australia . |
| 2052541-A | 4/1992 | Canada . |
| 4102427-A | 8/1992 | Germany . |
| WO 83/03189 | 9/1983 | WIPO . |

*Primary Examiner*—Vincent Millin
*Assistant Examiner*—Dinh X. Nguyen
*Attorney, Agent, or Firm*—Knobbe, Martens, Olson & Bear, LLP

[57] ABSTRACT

A surgical access device and method are provided for endoscopic surgeries comprising biopsies or other surgical cutting procedures. The device generally comprises a substantially rigid first channel associated with a first port and a second channel associated with a second port of a proximal housing. The first or main channel extends to a curved distal end of the device, and the second channel is connected to a guide channel extending tangential to the main channel. The guide channel comprises substantially noncompliant material and has a pre-insertion position such that a cross-section of an inserted portion of the device is substantially the same as a cross-section of the main channel. A preferred method of the present invention includes the use of an open-loop device formed at a distal tip of an introducer and an aspiration tube during the location, excision and removal of one or more tissue specimens.

25 Claims, 8 Drawing Sheets

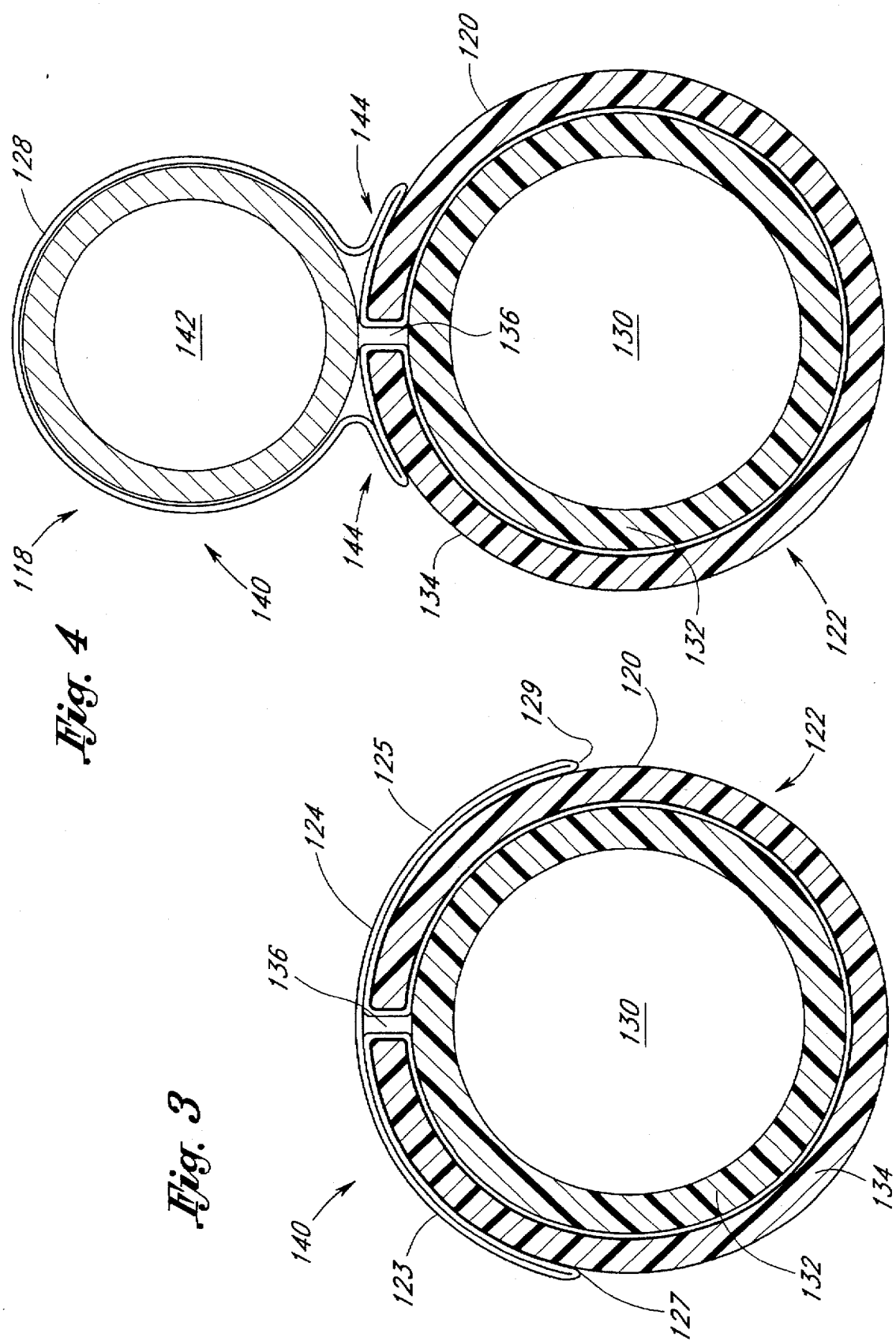

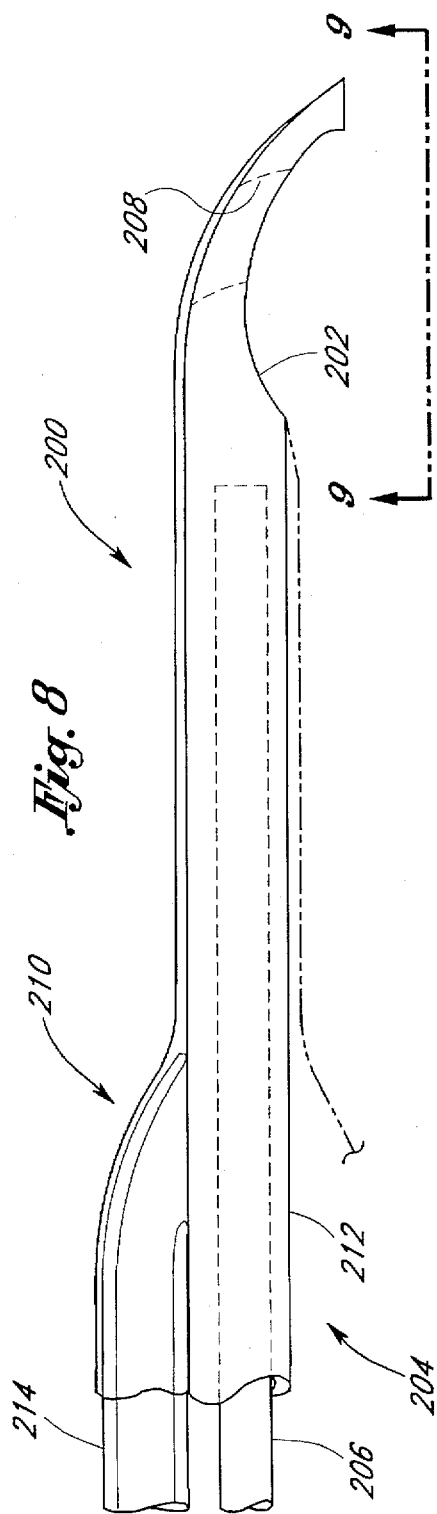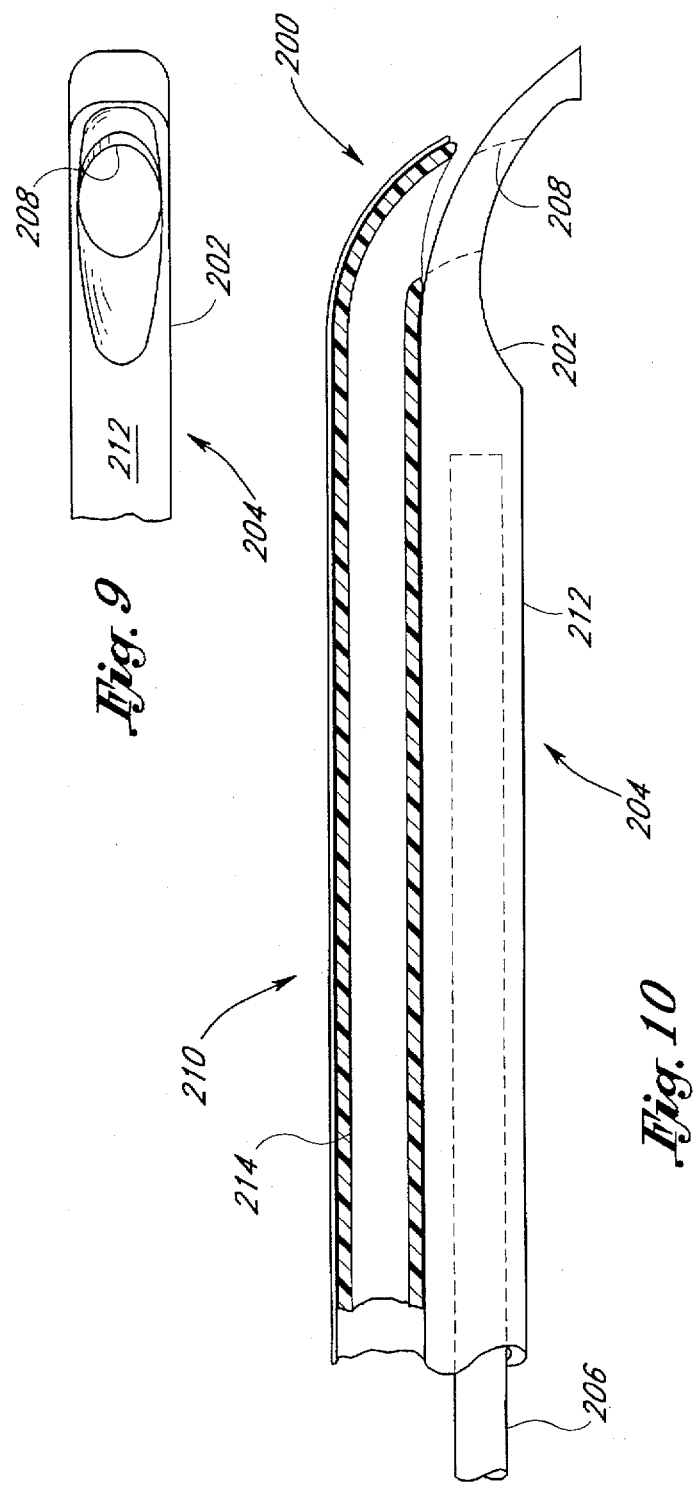

METHOD AND APPARATUS FOR PERFORMING BIOPSY

FIELD OF THE INVENTION

The present invention relates generally to surgical access devices for use in endoscopic surgery, such devices comprising introducers, endoscopic sheaths, catheters, endoscopes, cannulas and the like, and, in particular, to a surgical access device and method for performing biopsy or other surgical cutting procedures.

BACKGROUND OF THE INVENTION

The advantages of minimal invasion surgery are well known and understood. Essentially, through the use of advanced endoscopy and other vision systems, surgery can be performed percutaneously through one or more small incisions or portals formed in the patient's body or through a bodily orifice, such as vagina, cervix, urethra, rectum, mouth, etc. Entrance to the body is accomplished in a number of ways depending upon the type of procedure. Once a portal or "port" is formed in the patient's body, a number of surgical access devices may be placed therethrough in order to perform the endoscopic procedure. Such devices will typically include some form of endoscope or other vision system to allow the physician to visualize the procedure. However, other surgical access devices may be used in combination with an endoscope, such as an introducer, an endoscopic sheath, catheters, or other cannulas. Thus, endoscopes and other endoscopic surgical instruments may be inserted through these surgical access devices which may have one or more instrument channels formed therein. Such surgical access devices may be reusable and, thus, require sterilization (such as most endoscopes), or may be disposable (such as introducers, endoscopic sheaths, etc.).

Minimally invasive surgery obviously reduces the trauma and pain to the patient, accelerates recovery and shortens the average hospital stay, thus minimizing the costs of health care in the U.S. and around the world. In addition to minimal invasiveness, there is also a trend to attempt to perform unanticipated procedures during the initial surgery so as to avoid scheduling repetitive surgeries. That is, for example, frequently a diagnostic procedure is scheduled for a given purpose; however, once inside the patient, the physician notices a cyst, polyp, or other suspicious pathology. Therefore, the physician may desire to perform a biopsy or other surgical procedure. If an additional diagnostic or therapeutic procedure could be accomplished concurrently with the initial procedure, substantial savings in patient comfort, recovery time, and costs could be realized. However, presently in most cases, the patient must be rescheduled for a later procedure.

Although it is known in the prior art to provide auxiliary, expandable channels in surgical access devices, they have apparently not met with commercial success. A number of reasons may be postulated. That is, although it is understood that the surgical access device must initially have a small cross-sectional profile for ease of insertion, the means for expanding that device have varied. Typically, such expansion means comprises a secondary or auxiliary channel having a lumen for the insertion of an endoscope or other endoscopic instrument. Thus, the main lumen of the surgical access device is formed by a hollow channel defined by a certain wall of thickness. The cross-sectional profile of the surgical access device is usually circular, although other profiles have been utilized. As used herein, "profile" will mean a cross-sectional profile unless otherwise specified.

Thus, the goal of present access devices is to minimize their profile upon initial introduction. Following insertion, however, it is desirable to form a secondary channel in the device for the insertion of a second instrument in order to complete the intended procedure or another unanticipated procedure. This secondary channel is typically formed from a polymeric or rubberized elastic material. Due to their elastic nature, such secondary channels have substantial wall thicknesses. Moreover, in order to minimize the profile of the device upon insertion, these secondary channels must be collapsed in some fashion upon insertion. Thus, the cross-sectional wall thickness of the secondary channel must lie upon the outer diameter of the main channel, thus adding significantly to the overall profile of previous surgical access devices. This construction adds a new problem to the one the device is attempting to solve.

The most commonly proposed solution to the extra profile added by the secondary channel, is to surround it with an outer sheath or other elastic band, in order to hold it in a collapsed state around the outer diameter of the main channel of the surgical access device. However, this approach simply aggravates the problem due to the wall thickness of the outer sheath or banding. Moreover, these outer materials add to the radial resistance which must be overcome in order to push the instrument through the secondary channel. In addition, and quite significantly, the elastic nature of previous secondary channels presents severe frictional disadvantages, further intensifying the problem of instrument insertion. Moreover, in reusable systems, the outer sheathing or banding, which causes a secondary lumen to collapse, presents a substantial problem with respect to sterilization.

Another significant disadvantage of prior secondary channels is that they are elastically expandable, both longitudinally and radially. Thus, upon either insertion and/or deployment of secondary instrument, the channels may become loose or gathered. Thus, upon insertion of the instrument, there might be bunching or binding, which prevents the instrument from smoothly accessing its desired location. This requires the application of greater force on the instrument, thus increasing the pain and trauma to the patient which is intended to be avoided by the surgical access device. That is, most procedures of this type are performed on an out-patient basis with the patient undergoing only a local anesthetic. Thus, the difficulties associated with previous secondary channels, including their more frictional nature, increases the likelihood that the procedure will be uncomfortable and even traumatic for the patient.

Moreover, because of the elastic nature of previous secondary channels, they require an additional hollow tube to hold them in the open position for repetitive instrument insertion. Furthermore, there has been a lack of attention to leading edge design, so as to avoid contamination upon insertion of prior art surgical access devices. This is particularly a severe problem in connection with the usable systems which require sterilization between use.

Thus, there are substantial problems associated with secondary channels formed in a prior art surgical access devices. Moreover, previous devices have not addressed advances in endoscopic design, or more costly flexible endoscopes. That is, initially endoscopes were of the straight and rigid rod lens type. However, more recent semi-rigid endoscopes are smaller in diameter and allow some flexibility in use, unlike rigid scopes. Semi-rigid endoscopes present new obstacles, but also additional opportunities, with respect to auxiliary channels, which opportunities have not been addressed by previous surgical access devices.

With regard to biopsies and surgical cutting procedures, resectoscopes are commonly used for uterine and prostate surgery and generally comprise endoscopes with cutting and scraping tools built into their scope bodies. Cutting loops and wire configurations are presently available, and electrosurgical sources can be connected to other loop configurations and have rolling balls and blades. However, these devices are provided with only a single type of surgical function which is performed with the visibility provided by the endoscope.

Another biopsy device, specifically for dilation and curettage, comprises a channel for aspiration and a closed chamber on its curved distal end. This device generally corresponds to a rigid curette or scraping device.

Accordingly, there is a severe need in the prior art for surgical access devices and methods for use in performing biopsy or other surgical cutting procedures.

SUMMARY OF THE INVENTION

The present invention satisfies this need in the prior art by providing a surgical access device and method of its use wherein a secondary lumen of the device comprises a guide channel formed from an extremely thin, but very strong and substantially noncompliant membrane. This guide membrane exhibits performance characteristics which make it preferred for biopsies and other surgical cutting procedures.

Used for hysteroscopy, for example, a biopsy or cutting implement, such as biopsy forceps or a curette, may be inserted through either a rigid main channel or an expandable guide channel. A tissue specimen may then be trapped by the device or have an aspiration means to vacuum material from the body. A collection chamber provided exterior to the body is then used to retrieve the specimen.

In one preferred method of the present invention, a physician inserts an introducer constructed in accordance with the present invention into a port of the patient during endoscopic surgery. The guide channel of the introducer is in a pre-deployed arrangement, closely conforming to a lubricous top surface of the main channel. Optionally, distension media, such as carbon dioxide gas, may be supplied into the patient through the introducer. An endoscope is inserted into the main channel for viewing of the interior of the patient's body, with a curved distal end of the introducer providing a larger field of vision.

In the introducer of the present invention, the distal tip of the introducer may be provided with an open-loop. The open-loop forms a hole in the distal tip of the main channel further increasing the field of vision of the endoscope. An aspiration tube can be inserted into the guide channel, expanding the channel as it extends toward the distal tip for retrieval of a specimen which has been excised by a cutting instrument. An inboard configuration of the guide channel may be used for the introducer, wherein the guide channel is positioned on a generally concave side of the curved end of the introducer. Alternatively, an outboard configuration, with the guide channel on a generally convex side of the curved end of the introducer, may be used for this procedure. A sideboard configuration, with the guide channel on a lateral side of the main channel, is also possible.

The wall thickness of the membrane forming the guide channel in the present invention is so thin that it has only a negligible affect on the profile of the present surgical access device. This is true even though the membrane may be folded or doubled back on or around the outer wall surface of the surgical access device. Thus, the guide membrane of the present invention is compatible with very small diameter access devices which are more commonly being used with rigid and especially semi-rigid endoscopes. Accordingly, the surgical access device of the present invention is able to substantially reduce the pain and trauma associated with endoscopic procedures.

One important advantage of the present membrane is that it can be formed or set in position on the surgical access device. That is, by the use of moderate heat or other mechanical, adhesive or heat forming or heat shrinking techniques, the membrane can be "set" in order to closely conform to the outer surface configuration of the access device, thus maintaining a narrow or otherwise small profile. Moreover, outer elastic sheathing, straps, or binding of any type are unnecessary, thus, the profile of the access device is further minimized. An additional advantage of the present membrane is its lubricity. That is, the material in its natural state as formed on the access device is lubricous, thereby facilitating inserting of the access device and reducing discomfort.

The guide channel membrane of the present invention can be constructed from any one of a number of highly oriented or cross-linked, noncompliant materials, including, without limitation, polymers. Such polymers may preferably undergo an extrusion process in order to achieve their high orientation status, resulting in their noncompliant and substantially inelastic nature. Moreover, such extruded polymers are also very strong and tough and lubricous, as pointed out above. In the preferred embodiment, one die channel membrane material is polyethylene terephthalate ("PET"), although other materials within that group are possible, examples being polyolefins and their blends which can be highly orientated or cross-linked after radiation treatment and heat forming as found in the art of balloons for angioplasty catheters. Other materials include nylon and polyethylene which achieve orientation by pre-stretching, whereby the material has high strength and little elongation when a load (stress) is exerted upon it.

The guide channel membrane may be formed from material having various thicknesses, depending upon the application of the particular surgical access device; however, thicknesses in the range of 0.0005–0.002 inches are preferred. Thus, it can be seen that such membranes do not add significantly to the profile of the access device.

Another advantage of the guide channel membrane of the present invention is that they are "releasable" upon dilation. That is, although heat formed or otherwise set so as to closely conform to the outer configuration of the access device, the membrane material can easily open up or release to form a secondary guide channel. In most cases, dilation can be achieved by the secondary endoscopic instrument itself, without a need for a dilator or obturator. Thus, these additional steps can be avoided. Moreover, the materials are also internally lubricous, thus, minimizing resistance to instrument insertion and advancement. Since the membrane material is not elastic and is otherwise releasable, there is no radial resistance to instrument advancement. In addition, no internal support is necessary. That is, once the membrane material has been released, it forms a secondary channel which conforms to the nature of the tissue around it. In other words, if the tissue surrounding the access device and secondary channel is tight, the membrane will collapse and conform at the tissue in order to avoid unnecessary trauma. On the other hand, if the passage is expanded or dilated, the channel, following release, will maintain its general channel-like shape, without the need for any auxiliary internal tubing or support from any media such as fluid. Thus, the membrane will maintain its configuration, even with the instrument removed. In this regard, the membrane can be said to be "self-supporting," retaining its patentency characteristics.

The guide channel of the present invention is self-adjusting. That is, the membrane material will release to form a secondary channel which is only large enough to admit the passage of the instrument being advanced through it. Thus, the guide channel holds the instrument securely along its path as it is advanced to the distal end of the access device. This advantage also allows for insertion of instruments having various cross-sectional profiles, thus avoiding the need to design secondary channels specifically for certain instruments. In certain embodiments, perforations or slits may be formed in the guide channel in order to facilitate release or dilation.

As noted above, the guide channel membrane is distensible but substantially noncompliant. Thus, it will not expand elastically upon insertion or dilation, either longitudinally or radially. It will be understood that the term "radially" is intended to mean in an outward direction, the cross-sectional configuration of the present guide channel not being limited to a circular or cylindrical configuration. Thus, the guide channel will not bunch up or bind as the instrument is advanced through it. Moreover, because of its toughness and strength, repetitive insertions of the instrument without failure are readily achievable. The membrane will not experience longitudinal expansion, which could result in the guide channel extending beyond the distal end of the introducer, thereby blocking or obscuring vision of the endoscope. Upon withdrawal, the guide channel membrane is easily collapsible so as to minimize any pain or trauma. Moreover, with the application of a slight vacuum, the membrane will conform closely to the outer surface configuration of the surgical access device for easy withdrawal.

The surgical access device of the present invention can be constructed from inexpensive materials and in accordance with simple construction techniques. This is particularly true of the guide channel membrane. Thus, the access device is disposable, thus avoiding problems associated with sterilization. Moreover, the membrane is compatible with any type of surgical access device, including, for example, introducers, endoscopic sheaths, catheters, cannulas, and endoscopes themselves.

In accordance with another advantage of the present invention, one embodiment of the membrane described above is used to form a guide channel on the surgical access device. Unlike secondary channels of the prior art, the present guide channel can be used to guide an instrument through a bend or curve as may be experienced in a procedure using a semi-rigid endoscope. In other words, such endoscopes are often used in connection with curved introducers which allow them to navigate certain curved anatomical paths and/or to move tissue. Thus, in accordance with one aspect of the present invention, the guide channel is nonlinear. Such channel can be formed upon a guide platform which is formed on or is otherwise associated with the access device. Moreover, guide rails can be formed to further provide structure and rigidity to the secondary channel. The bends or curves formed in the guide channel to orient the secondary lumen so that the instrument can arrive at a specific distal location with respect to the primary lumen, depending upon the procedure. The guide platforms or rails can take on a number of configurations. Advantageously, however, due to the formable and thermoplastically settable nature of the channel membrane, the channel membrane can be folded or arranged with respect to the access device in a wide variety of ways.

The surgical access device of the present invention also exhibits a particular distal end design which avoids contamination. Upon insertion of the device, the instrument channel is sealed so as to avoid entry of tissue or foreign contaminating material. Due to the thermoplastic nature of the channel membrane, the seal can be accomplished by heat forming the channel at the distal tip. Alternatively, a narrow profile tip can be designed which plugs the distal opening of the secondary channel while still facilitating entry of the access device. Like the distal end of the present access device, the proximal end also features a particular "y" design which facilitates advancement of a secondary instrument into the guide channel while minimizing risk of damage to the device or discomfort to the patient. The proximal end of the access device is provided with a housing which gently introduces the instrument along a path which eventually becomes tangential to the main longitudinal axis of the access device. The housing which surrounds the proximal end is also provided with appropriate valves to control and regulate the in-flow and out-flow of distension media, irrigation fluid, or other fluid.

As noted above, the guide channel of the present invention can be integrally formed on the insertion tube of an endoscope or separately formed on an introducer, endoscopic sheath, and the like. In the latter case, the introducer can be designed and constructed so as to guide the entrance of the secondary instrument in a particular way in order to achieve a specific purpose, depending upon the procedure being accomplished. Moreover, the instrument can enjoy lumen independent of any movement of the endoscope which is inserted through the main channel of the introducer. The settable nature of the membrane material facilitates a number of construction arrangements and techniques. Thus, the membrane material can be folded or stored with respect to the access device on an exterior surface, interior surface, or other intermediate location. It can be coupled to the access device by a wide variety of means, including mechanical, adhesive, heat formation, etc.

The surgical access device of the present invention is preferably constructed from a main tube which provides a main channel for the access device. Typically, the main channel provides access for insertion or introduction of an endoscope; however, other instruments can be introduced into the patient as well through the main channel. The guide channel membrane is formed onto the main tube in the following manner. The membrane is provided in the form of a hollow tube, which is typically extruded to form that shape, so as to have a outer diameter which is greater than that of the main tube. The membrane can be constructed from PET tubing which can come in the form of balloon tubing which is pre-stretched and highly orientated for minimal elongation. Other constructions of membranes can use polyolefins and their blends, polyethylene and nylons which are highly orientated or cross-linked. The guide channel membrane tube is placed over the main channel tube and positioned eccentrically with respect to the axis thereof.

A split tube sheath is mechanically clamped over the main tube capturing the guide channel membrane tube against the main tube. The split sheath can be made from nylon 11 which has a high strength with little wall thickness. Other materials such as polycarbonate, polyethylene, urethane, and the like, can be employed. The split sheath can be mechanically fixed to the main tube or placed onto the main tube by a variety of adhesive agents or thermal bonding techniques. The actual width of the slit itself can vary, which will affect the profile of the membrane channel. The excess membrane material, owing to the fact that its outer diameter is greater than that of the main tube, is allowed to escape through the slit in the sheath and extends outwardly therefrom. This excess material is then folded, pleated or otherwise stored with respect to the main tube in any one of a variety of ways so as to minimize the profile of the surgical access device. Typically, the excess membrane material is folded or doubled back on itself so as to closely conform to the outer surface configuration of the tube. An intermediate amount of heat, such as approximately 160° F., is then applied to the membrane material so as to heat form or set it in position closely conforming to the main tube, although other mechanical forming or adhesive techniques may be employed.

In an alternative introducer embodiment, an even narrower profile introducer can be constructed without the need for an outer split sheath. In this case the guide channel membrane tube is heat bonded or otherwise coupled directly to the hypotube by adhesive or other means. To facilitate this construction, the membrane tube can be supplied in a multi-lumen or FIG.-8 configuration, wherein the membrane is constructed from an extrusion or other process. Moreover, one or more of the lumens may be collapsible, and the others may be noncollapsible, either due to their increased wall thickness or to rigidifying means such as hypotubes or reinforcement devices, etc.

In the preferred embodiment of the surgical access device of the present invention, a merge channel is formed along the main channel in order to provide for the easy insertion of a secondary instrument into the guide channel. The merge channel can be constructed from a variety of materials including nylon 11 and other polymers, as well as stainless steel which can be flexed yet retain radial integrity. As noted above, the merge channel is proximally located with respect to the surgical access device and remains substantially out of the body. In accordance with the present method, the merge channel tube is longitudinally aligned with respect to the axis of the main tube prior to the over-wrapping of the guide channel membrane tube. Thus, the proximal end of the membrane tube circumscribes both the main tube and the distal end of the merge channel tube and the guide channel is simultaneously formed around both the main tube and the merge channel tube to comprise the "y" junction of the surgical access device. To provide mechanical strength at this y junction, a housing or other mechanical clamping means is provided. The housing can take a variety of forms to provide ergonomic benefits to the operator or clinician. In construction, it can be made from a variety of injection-molded plastics including polycarbonate, polysulfone, nylon, etc., or it may be machined. It can be a part of the disposable introducer or a reusable separate unit which is re-sterilized and placed back onto the surgical access device by the operator prior to each use.

The distal tip of the surgical device is preferably sealed so as to prevent contamination or distortion of the guide channel upon insertion of the access device into the body. Likewise, at the proximal end of the access device, the main channel and merge channel are provided with the necessary valving for irrigation or distension media. The valving must prevent any leakage around an instrument or endoscope when these devices are placed through the ports and typically includes an O-ring or washer type structure. In addition, they must contain structures such as duck-bill or star valves which prevent the backflow of media through the ports when no instrument or endoscope is through the port. These valves can be made from silicone, rubber and other elastomeric materials which are known to those skilled in the art.

Thus, in summary, the present invention generally comprises an apparatus and method of obtaining a tissue specimen from a patient during endoscopic surgery, a surgical access device being provided which has a substantially rigid main channel and an expandable guide channel. The guide channel initially has a pre-deployment, or pre-insertion, position such that a cross-section of an inserted portion of the device is substantially the same as a cross-section of the main channel, the device having a curved distal end. A port is established in the patient for entry of the device, as either an orifice or incision, and the device is inserted into the port with the guide channel in its first position to facilitate entry into the patient's body and thereby minimize patient discomfort.

An endoscope is inserted through one of the channels for viewing therethrough, and the device is positioned according to visual information obtained from the endoscope in order to locate a desired tissue specimen. The tissue specimen is removed from the patient, and the device is removed from the port in the patient. The various insertions and removals of the instruments during the surgical procedure are facilitated by a merge channel at a proximal end of the device and the noncompliant nature of the material forming the guide channel, the guide channel being self-adjusting to a diameter of the instrument inserted therethrough. Advantageously, the introducer's main and guide channels in the present invention may each be used with a plurality of instruments for performing several surgical functions during a single surgical procedure.

Accordingly, a surgical access device and method of the present invention provide a substantial advancement over the prior art.

BRIEF DESCRIPTION OF THE DRAWINGS

FIG. 3 is a cross-sectional view of the access device taken along line 3—3 of FIG. 2 illustrating the main channel and guide channel in their initial state upon insertion of the access device into the body and prior to deployment of a secondary instrument through the guide channel.

FIG. 4 is a cross-sectional view of the access device taken along lines 4—4 of FIG. 2 illustrating the guide channel of the present invention in a released or expanded state as the secondary instrument is advanced therethrough.

FIG. 8 is an elevational view along the longitudinal axis of the distal end of a preferred embodiment of the present invention comprising an introducer having an open-loop formed thereon.

FIG. 9 is a cross-sectional detail view of the open-loop of FIG. 8 showing a hole formed therethrough.

FIG. 10 is a cross-sectional view showing the open-loop introducer with an aspiration tube positioned in the guide channel.

DETAILED DESCRIPTION OF THE PREFERRED EMBODIMENT

Figure 1:
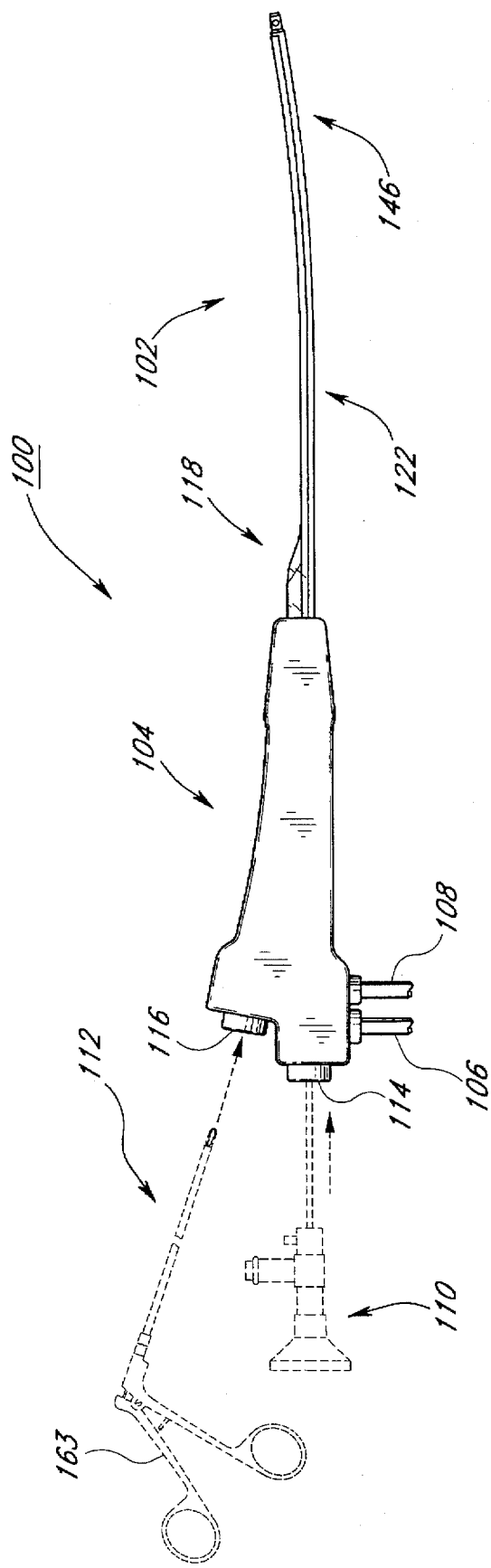
FIG. 1 is a side view of the surgical access device of the present invention illustrating a partially inserted endoscope and a secondary instrument in a pre-introduction location.

With reference to FIG. 1, there is shown the surgical access device 100 of the present invention. In this case, a surgical introducer has been selected to illustrate the principles of the present invention; however, it will be understood that such principles apply equally to all types of surgical access devices, as well as to devices not necessarily limited to surgical access. In the broadest sense, the principles of the present invention encompass devices where secondary channels or other types of guide channels, expandable or otherwise, are desirable or necessary in order to allow passage of some type of instrument. Such devices include without limitation introducers, endoscopic sheaths, catheters, cannulas, and the like. The secondary or guide channels of the present invention may be retro-fitted onto such devices or integrally formed therein. For example, the guide channel of the present invention may be integrated into the insertion tube of an endoscope itself.

Furthermore, it will be understood that the present invention is compatible with all types of instruments, including catheters, obturators, etc. Also, visualization devices used with the present access device are not to be limited to endoscopes, but also include all types of such devices, including fluoroscopes, etc. Thus, the terms "instrument" and "endoscope" are intended to be only illustrative and representative of the wide variety of devices that can be utilized in accordance with the present invention, and such terms are not intended to be limiting in any respect.

Thus, the fact that the present invention is described with respect to an introducer is illustrative only and not intended to be limiting in any respect.

Surgical Introducer

Thus, with further reference to FIG. 1, there is illustrated a surgical introducer 100 into which the principles of the present invention have been incorporated. In this case, the introducer 100 is intended for gynecological procedures, such as hysteroscopy or cystoscopy; however, again, a wide variety of procedures may be performed with the surgical access device of the present invention.

As shown in FIG. 1, the access device 100 comprises a distal insertion portion 102, which is intended for insertion into the patient's body, and a proximal housing portion 104, which generally remains outside of the patient's body. In this case, access to the patient's body is achieved through dilation of the cervix; however, in other procedures, access may be gained through other natural openings in the body or by surgical incision, etc. The details of construction of the insertion portion 102 are described below in more detail and illustrated in connection with FIGS. 3 and 4, while the details of the housing portion 104, including the in-flow and out-flow conduits 106, 108, are described and illustrated below in connection with FIG. 6.

To the left of the proximal housing portion 104 shown in FIG. 1, there is shown in exploded relationship to the introducer 100 an endoscope 110 and a secondary instrument 112, in this case a grasper which can be used for the removal of foreign bodies or tissue. It is understood that biopsy forceps or curettes, or other such excising instruments may alternatively be inserted into the introducer 100. The endoscope 110 is shown partially inserted into a main port or endoscopic port 114 formed at the proximal end of the introducer 100. The secondary instrument 112 is shown positioned prior to insertion into a secondary port or instrument port 116. The terminology of main or endoscopic port 114 and secondary or instrument port 116 is merely illustrative since the endoscope 110 is typically inserted into the main port 114 of the introducer 100, while the secondary instrument 112 is inserted through an auxiliary or secondary port 116. However, in accordance with the principles of the present invention, this arrangement can be reversed, or any other of a wide variety of instruments may be used in connection with the various ports of the access device 100. In addition, multiple ports in addition to two may be formed on the introducer, depending upon the nature of the procedure to be performed.

FIG. 1 illustrates the introducer 100 prior to and upon insertion into the patient's body, but prior to insertion of any secondary instrument. Although not readily apparent from FIG. 1, a guide channel 118 of the present invention is mounted and formed on an exterior surface 120 of an endoscopic channel 122 which forms the basic cross-sectional profile of the insertion portion 102 of the introducer 100. Since the secondary instrument 112 has not yet been inserted through the instrument port 116 or through the proximal housing 104 to the insertion portion 102, the guide channel 118 for the instrument is virtually unnoticeable to the eye or touch. Thus, as illustrated in FIG. 1, the guide channel 118 adds only a negligible dimension to the profile of the access device 100, thus minimizing pain and discomfort to the patient. This is a particular advantage in gynecological procedures which are frequently performed on an out-patient basis and under only a local anesthetic. Thus, if a secondary procedure proves unnecessary, there has been no unnecessary discomfort or pain to the patient since the profile of the introducer 100 has been minimized. However, if such a secondary procedure becomes necessary, it can be readily accomplished with only a minimal intrusion into the body through the existing port, without the need to schedule a second surgery. It also has the obvious advantage of not requiring a pre-dilatation step prior to the insertion of the introducer. In some cases, such as for the cervix, dilatation of the cervical canal can be painful to the patient and should be minimized as much as possible. In addition, the uterine cavity requires distension to allow for proper visualization. If the cervix is over-dilated during the pre-dilatation step, excessive cervical leakage can occur when trying to distend the uterus. Thus, the introducer 100 with its guide channel 118 and low profile will minimize pre-dilatation of the cervix and will provide a guide channel having the diameter of the instrument being used, thereby reducing the leakage potential via an over-dilated cervical canal.

It will be noted from FIG. 1 that the guide channel 118 closely conforms to the outer configuration of the endoscopic channel 122 without the need for outer sheaths or bands which would increase the profile thereof. Moreover, since the guide channel 118 is formed on the exterior of the endoscopic channel 122, its natural lubricity provides an important advantage in connection with the ease of insertion of the introducer 100. However, it will be noted in accordance with the present invention that the guide channel 118 may also be formed on or within the endoscopic channel 122 in other configurations with respect to the introducer 100. Moreover, multiple guide channels may be formed on or incorporated into the main or endoscopic channel 122.

Figure 2:
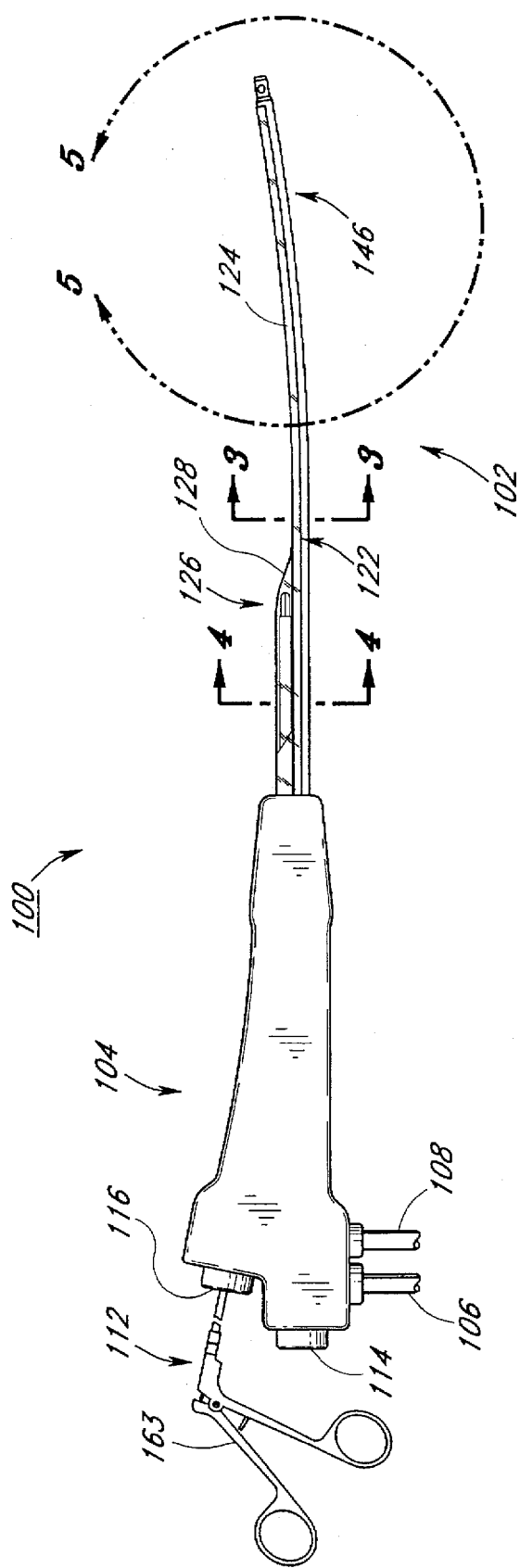
FIG. 2 is a close-up side view of the access device illustrating the advancement of the secondary instrument through the guide channel of the present invention.

FIG. 2 is a view of the introducer 100 of the present invention illustrating the deployment of the secondary instrument 112 as it advances along the guide channel 118. In this FIG. 2, a portion of the guide channel 124 ahead of the instrument 112 is folded over and upon the insertion portion 102 of the introducer 100. The characteristics of the guide channel 124 at this location are described below in more detail in connection with the description of FIG. 3. However, in the region of a leading edge 126 of the instrument 112, a guide channel portion 128 is shown to be releasing its insertion position and gradually expanding so as to allow the instrument 112 to advance. It will be noted that, although FIG. 2 shows expansion or dilation to be achievable by the use of the secondary instrument itself, other instruments, hollow tubing, media, or means are equally available to achieve expansion in accordance with the guide channel 118 of the present invention.

As the instrument 112 advances, the guide channel 118 gradually releases in order to maintain the minimum profile of the introducer 100. Thus, pain and discomfort to the patient are minimized. Furthermore, the surgical access device 100 of the present invention makes it possible for more endoscopic surgical procedures to be conducted on an out-patient basis with only minimal or local anesthesia.

Such procedures would include those which are planned and scheduled, as well as secondary procedures which are unanticipated. In other words, a physician may enter a patient's body endoscopically for the purpose of a particular, planned diagnostic or therapeutic purpose. Initial insertion of the introducer 100 is typically accomplished under the visual guidance of the endoscope 110. However, once inside the patient's body, under these visual conditions, it may become necessary or desirable to perform a secondary procedure using a secondary instrument inserted through the instrument port 116 and advanced through the proximal housing portion 104 and into the guide channel 118 of the present invention. Thus, regardless of the initial purpose of the endoscopic procedure, this secondary procedure can be performed virtually simultaneously without rescheduling a second procedure. Moreover, the secondary procedure can be performed with only minimal discomfort to the patient and without withdrawing or reinserting the endoscope 110 or any other instruments. Because of the narrow profile of the present access device 100, a wide variety of primary and secondary endoscopic procedures (as well as multiple procedures of all types) can be safely and efficiently performed on an out-patient basis. Thus, the high cost of health care can be contained somewhat.

Guide Channel

An important feature of the present invention which allows these advantages to accrue is the guide channel 118 of the introducer. This guide channel 118 can be described in more detail in connection with the cross-sectional drawings of FIGS. 3 and 4.

FIG. 3 is a cross-sectional view of the insertion portion of the introducer 100 at a location ahead of the advancing instrument 112. FIG. 3 illustrates the main or endoscopic lumen 130 for the insertion of the endoscope 110 or other instrument (although, the endoscope is not shown in FIG. 3 for clarity of illustration). This lumen 130 is formed by the endoscopic channel 122 which may comprise a tube 132 of various constructions. The endoscopic tube 132 is in turn surrounded by a larger diameter split tube or sheath 134. A split in the sheath 134 defines a slit or longitudinal opening 136. Sandwiched between the inner endoscopic tube 132 and the outer split sheath 134 is a membrane 140 which forms the present guide channel 118. This membrane 140 can initially be formed in the shape of a tube or have other construction.

As shown in FIG. 3, the membrane 140 surrounds the inner endoscopic tube 132 but, due to its greater diameter, also extends out of the longitudinal opening 136 in the split sheath 134. This excess membrane material may be folded back onto the outer surface 120 of the split sheath 134 to form a double-layer of the membrane 124 along a partial circumference of the introducer 100. Likewise, the folding pattern of the pleats may be such that all of the pleat is on one lateral side of the introducer or the other, rather than the two equal pleats shown in FIG. 3.

This pleated or folded-back portion 124 shown in FIG. 3, forming pleats 123, 125, is that portion which defines the guide channel 118 for the instrument 112, as illustrated in more detail in FIGS. 2 and 4. As illustrated in FIG. 3, prior to instrument deployment, the guide channel 118 is defined by the membrane 140 which closely conforms to the outer surface 120 of the split sheath 134. For example, the lateral edges of the pleats 123, 125 can be provided with thin creases or seams 127, 129, which can be formed and set in the membrane material. Thus, the narrow profile of the introducer 100 is maintained. In addition, because of the close conformity of the guide channel membrane 140, it is less likely to be distorted or disturbed upon insertion of the introducer 100 into the body. Thus, the guide channel 118 maintains its structural integrity and avoids patient discomfort even before insertion of the secondary instrument.

The membrane 140 which comprises the guide channel 118 can be extremely thin, ranging in thickness between 0.0005" and 0.002", preferably being about 0.001". Thus, even when doubled back on itself and lying on the outer surface 120 of the split sheath 134, the guide channel 118 adds only a negligible thickness to the profile of the surgical access device 100. Moreover, the guide channel 124 in its pre-release position shown in FIG. 3 will hold a set in this position and does not require any external elastic sheets or strapping to bind it in position on the introducer 100.

It will be understood, as noted above, that the present guide channel 118 can be formed on or in connection with surgical access devices of a wide variety. Moreover, in its pre-release position 124 (which it assumes prior to and even during insertion of the access device 100 into the body, but prior to deployment of an instrument through the guide channel 118), the guide channel 118 can be stored, wrapped, or folded in a number of configurations, other than that shown in FIG. 3.

For example, the membrane 140 may comprise multiple pleats or folds which will facilitate a larger guide channel. The membrane 140 can alternatively follow a multitude of folding patterns which preferentially unfold upon the exerted force of the insertion element. The additional material which constitutes these multiple folds will allow for larger instruments to pass through the guide channel 118.

Figure 5:
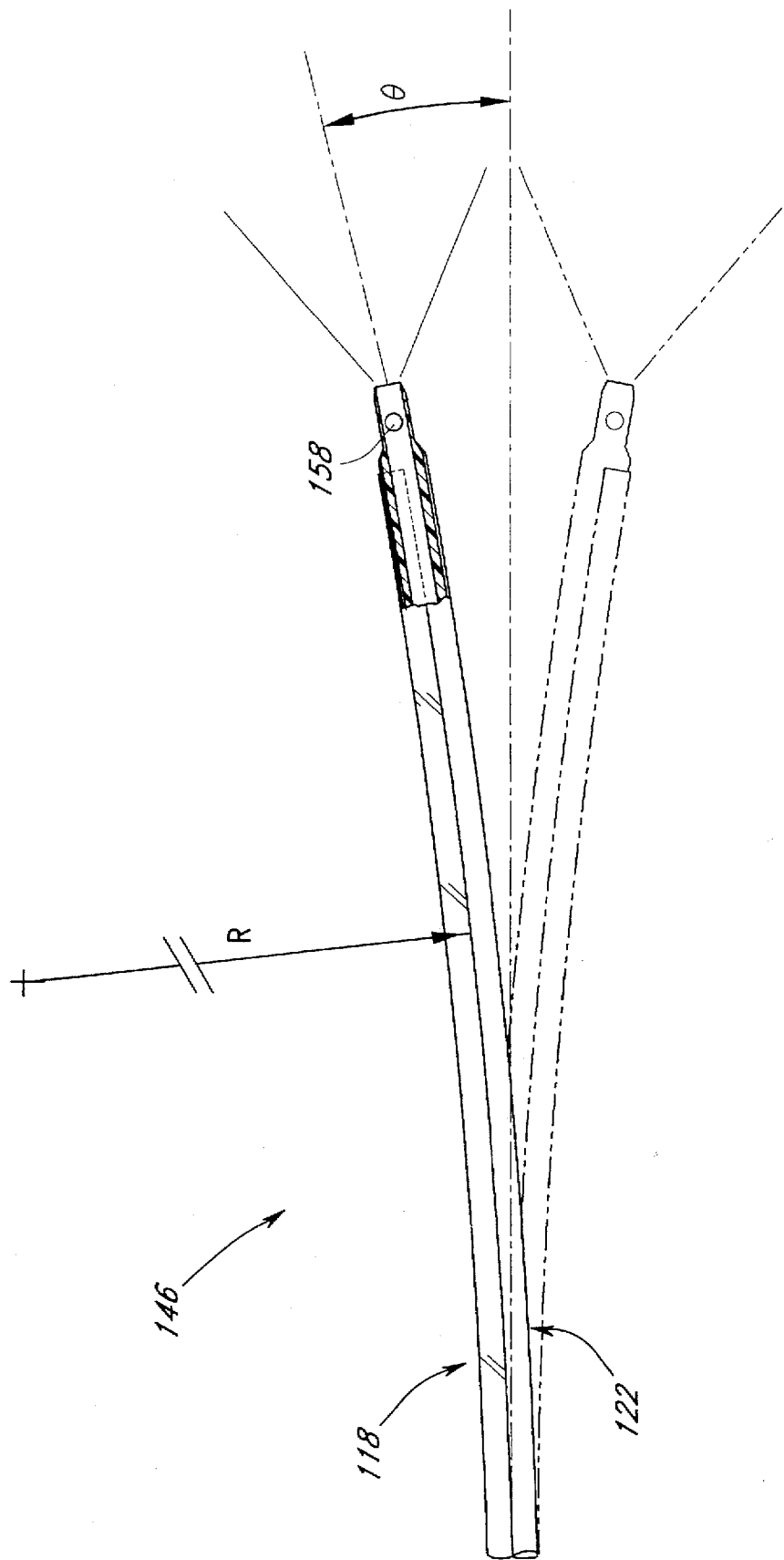
FIG. 5 is a close-up perspective view of the distal tip of the present access device illustrating a bend or nonlinear curve which may be formed in the device, and further illustrating the manner in which the present guide channel allows a secondary instrument to conform to such curve.

It will be understood that the endoscopic tube 132 of FIG. 2 can be constructed from a wide variety of materials which provides rigidity and protection for the endoscope 110. Preferably, such tube 132 can take the form of a stainless steel hypotube. Thus, the tube 132 can provide the rigidity necessary for initial insertion, and can be used to move tissue without fear of damage to the endoscope 110 within. Moreover, the endoscopic tube 132 can take on a bend or curve, as illustrated in FIG. 5, to facilitate a particular procedure. With advancements in rigid and semi-rigid endoscopes, such curves or bends in introducers can facilitate intricate navigational procedures while not damaging the endoscope. The curves and bends also direct the visualization area of the endoscope to preferentially view anatomical structures not on the axis of the insertion point in the body.

The outer split sheath 134, in its typical construction, is smooth and lubricous in order to facilitate insertion of the introducer 100. It may be constructed from a durable, biocompatible polymeric material, such as nylon. Preferably, nylon 11 can be utilized. It will be noted in connection with FIG. 3 that typical introducer construction will include both the endoscopic tube 132 and the outer nylon layer 134. Thus, the guide channel 118 of the present invention does not significantly increase the profile of such an access device 100. In this connection, a number of cross-sectional introducer configurations will be readily apparent to those of ordinary skill in the art, including non-circular configurations. In addition, a wide variety of endoscopic tube and split sheath wall thicknesses are within the realm of the person of ordinary skill; however, preferably, the endoscopic tube 132 would have a wall thickness of approximately 0.008 inches, while the split sheath 134 would have a wall thickness of approximately 0.005 inches.

On the other hand, the versatility of the guide channel of the present invention allows it to be incorporated into introducers of even narrower profiles. For example, in an alternate embodiment of the membrane (not shown), the outer split sheath for capturing a guide channel membrane onto a tube is eliminated by having the membrane heat bonded or otherwise coupled to the tube by adhesive or other means. To facilitate this construction, the guide channel membrane can be supplied in a multi-lumen or FIG. 8 configuration, with one lumen of the membrane being mounted on the tube, leaving a second lumen to be folded or pleated thereabout to provide a guide channel in its stored position. It will also be noted that guide channel membranes having multiple lumens can be provided and mounted on the main channel tube in this or another manner, and then folded and set in position about the tube in order to provide an introducer with extremely narrow profile. Thus, three, four, or more membrane tubes can be mounted, either jointly or separately, on the introducer so as to provide multiple lumens. In addition, one or more of the tubes (which can be constructed from an extrusion or other process) may be collapsible, while others may be noncollapsible, due either to the wall thickness of the membrane extrusion or some other rigidifying or reinforcing mechanism (such as a hypotube or the like).

With reference to FIG. 4, there is shown cross-sectional view of the present introducer 100 through the insertion portion 102 where the instrument 112 has already advanced. In this case, the instrument 112 is shown almost completely occupying a lumen 142 defined by the guide channel 118 of the present invention. As shown in FIG. 4, the guide channel portion 128 is shown releasing its pre-deployment position to allow the instrument 112 to easily pass along the guide channel 118 and into the patient.

The guide channel 118 of the present invention may be constructed from a membrane 140 which exhibits a number of advantageous characteristics. For example, in addition to its external lubricity, the membrane 140 is also internally lubricous to facilitate the deployment of the instrument 112. The physical characteristics of the membrane 140 also allow the guide channel 118 to be self-adjusting. That is, as shown in FIG. 4, the guide channel 118 releases only to the extent necessary to accommodate the particular instrument being inserted through it. If not needed, the membrane 140 remains folded in its set position in the region indicated by the arrows 144 of FIG. 4. These advantageous characteristics allow the guide channel 118 to accommodate a number of instruments of various cross-sectional dimensions without significantly increasing the profile of the introducer 100.

Likewise, if the instrument 112 is removed from the guide channel 118, the membrane 140 causes it to maintain approximately the same position as it did with the instrument 112 inserted within, thus facilitating reinsertion of the same instrument, or, if necessary, another instrument. For instance, in the case of removing multiple portions of tissue from the body, it may be necessary to remove tissue and then reinsert the instrument 112 back through the guide channel 118 to remove more tissue. Thus, there is no radial resistance to reinsertion which reduces the risk of damage to the guide channel 118 and discomfort to the patient. If the instrument 112 is withdrawn upon completion of the procedure, the guide channel 118 is readily collapsible for withdrawal of the introducer 100 so that pain or trauma to the patient is avoided. Also, if desired, the guide channel 118 can be evacuated of fluids or such in order to facilitate its collapse prior to withdrawal.

As noted above, the guide channel membrane 140 is noncompliant both longitudinally and radially. Thus, it does not exhibit elastic characteristics which might cause the guide channel 118 to bunch up or bind as the instrument 112 is advanced therethrough. Moreover, the guide channel membrane 140 is malleable, meaning that it tends to conform to the pressures and forces exerted upon it by ambient conditions, including surrounding organs, bodily fluids and other media. This feature advantageously tends to reduce resistance to movement of the access device 100 and enhance patient comfort. On the other hand, in the absence of such ambient forces, the membrane 140 maintains its position and configuration, having somewhat of a "memory" in this regard.

A number of materials can achieve these advantages of the guide channel membrane 140 of the present invention. For example, inelastic polymers or other pleated, woven, or braided materials can be utilized. Preferably, however, highly orientated or cross-linked, noncompliant polymers can be utilized as a guide channel membrane material. Such materials tend to be thermoplastically settable, with glass transition temperatures greater than room temperature. In addition, such polymers are semicrystalline and deformable in the crystalline state. One preferred example of such a polymer is polyethylene terephthalate ("PET"), although other polymers are possible. For example, polybutyl terephthalate may be utilized as a guide channel 118 as well as nylon 6 or nylon 66. These materials, as well as others, exhibit the advantages described above. In one preferred embodiment, the PET material which comprises the guide channel membrane 140 has a glass transition temperature of 180° F. Thus, the setting temperature used in constructing this access device 100 is preferably about 160° F. It will be noted in this regard that sterilization of the device 100 is achieved at about 140° F.

Figure 11:
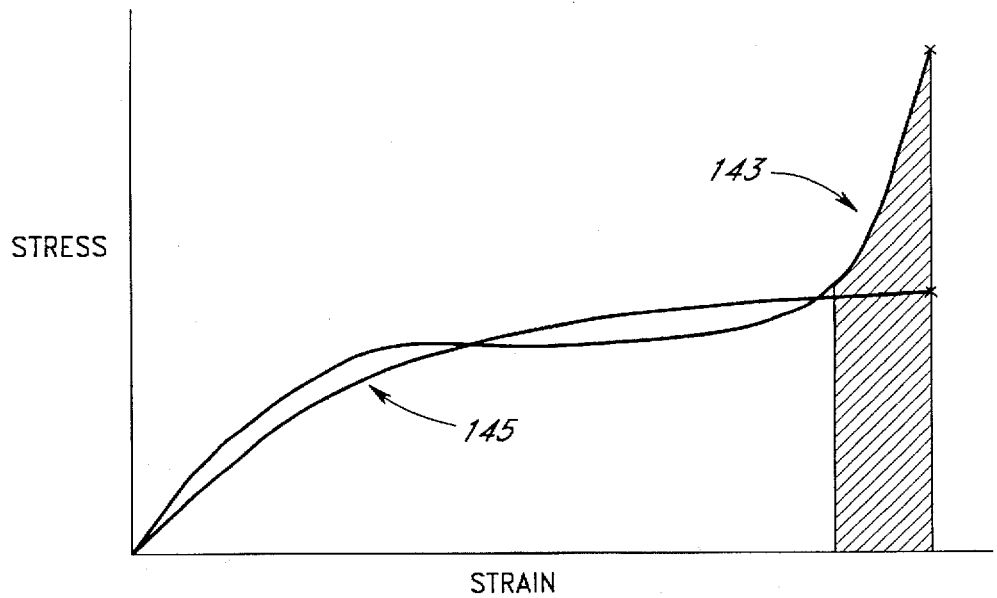
FIG. 11 is a graph illustrating the stress-strain relationship of oriented PET, as used for the guide channel membrane, in comparison with a typical elastomer.

In the case of PET, FIG. 11 illustrates the noncompliant (stress/strain relationship) of oriented PET as compared with a typical elastomer. A PET curve 143 in the graph shows a shaded region which depicts the behavior of a highly-orientated PET which has been pre-stretched. These stress-strain properties relate to a material which has high strength and very little elongation when a load is exerted upon it. Conversely, an elastomer behaves different in this and all sections of its curve 145 on the graph by elongating with little additional stress. Thus, where careful precision in the configuration of the guide channel is necessary, membrane material such as PET is advantageous.

Figure 12:
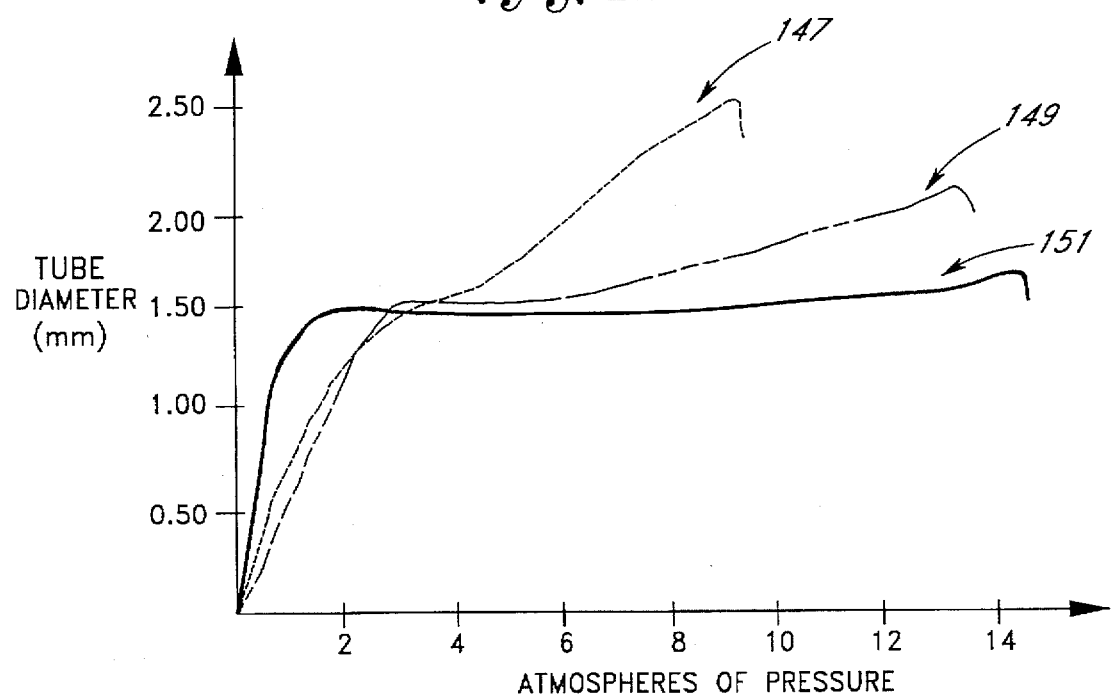
FIG. 12 is a graph illustrating the relationships between tube diameter and internal pressure for tubes comprising PVC, polyolefins, and PET material.

In addition, FIG. 12 illustrates the relationships between tube diameters and internal pressure for tubes comprising PVC 147, polyolefin 149 and PET material 151. In the graphs in FIG. 12, plots are shown for a closed vessel structure such as a balloon for various materials in which the outer diameter measurement is plotted versus the internal pressure applied. In this example, the PET material 151 demonstrates very little distension with greater internal pressure as a result of its high strength and low elongation in comparison to the polyolefin and PVC materials 149, 147 used for this example. Nevertheless, these and other materials can provide suitable guide channel membranes if treated properly during their manufacturing process. Thus, a major component of the inelastic behavior of PET and polyolefins is the fact that their polymer chains in the material have been highly orientated (PET) or cross-linked (polyolefins) with each other, providing greater strength and resistance to strain. This high degree of orientation, either by processing or secondary operations such as radiation treatment or forming an axial stretching, enables the nondistensible behavior of the present guide channel membrane.

Curved Guide Channels

FIG. 5 illustrates another advantage of the present guide channel 118 relating to its ability to actually guide a rigid or semi-rigid instrument 112 being deployed through it along a curved path. This advantage can best be described in light of the following background information. As shown in FIG. 1, a distal end 146 of the introducer 100 of the present invention is curved slightly. This curvature provides certain advantages, depending upon the endoscopic surgical procedure being performed. In this case, the introducer 100 of FIG. 1 can be used in performing a hysteroscopy, wherein a angle of θ curvature in the range of 5–150 in the access device 100 is advantageous in navigating the uterine canal. This curvature, as noted above, can also be used to gently move tissue out of the way in order to achieve advancement of the endoscope-introducer combination 110, 100 to the desired location. With recent advancements in endoscopes, curvatures in these ranges, even up to 30°, can be achieved without damage to the optical systems of the endoscopes.

However, another advantage of a curved introducer 100 is illustrated in FIG. 5. As shown therein, an endoscope 110 which provides vision out of the curved distal end 146 of the introducer 100 is able to sweep out a larger field of vision upon rotation of the introducer 100. This is illustrated in FIG. 5 by a first and second position (in phantom) of the distal end 146, rotated 180 degrees apart. This is a particular advantage in the case of rigid or semi-rigid endoscopes which do not have articulation means mounted at the distal end. In order to achieve this degree of curvature, as noted above in connection with FIGS. 3 and 4, the endoscopic tube 132 can be constructed from a strong and rigid stainless steel material which can be preformed or bent to the desired curvature. While this material will provide the rigidity, strength, and protection for the endoscope, it does not in and of itself solve the problems of secondary channels formed in such curved surgical access devices. Thus, secondary channels of the prior art were constructed to be used only with straight instruments or flexible instruments, such as catheters.

The guide channel 118 of the present invention accommodates a rigid or semi-rigid instrument 112 which experiences a curve along its shaft as it is inserted through the guide channel 118. Thus, the guide channel 118 of the present invention makes possible another category of endoscopic surgical procedures requiring a curved but rigid or semi-rigid instrument. First, as noted above, the guide channel membrane 140 is constructed from an extremely strong material in order to withstand the stresses on it caused by a biased instrument mounted therein. Nonetheless, it is important that the secondary instrument 112 being advanced through the guide channel 118 is provided with a smooth and straight passage. Any slippage or lateral movement may cause damage to the guide channel 118 and/or discomfort to the patient.

Moreover, the guide channel 118 may be located at a number of different circumferential locations with respect to the main or endoscopic channel 122. Thus, as shown in FIG. 5 in phantom, the guide channel is located at the bottom of the main channel curvature. This longitudinal location may be considered "inboard" with respect to the curvature of the introducer 100. That is, the guide channel may be located on a generally concave side of the main channel curvature. However, the guide channel 118 may also be positioned, as needed or desirable for a particular procedure, "outboard" of the introducer curvature or on a generally convex side of the introducer 100; or, alternatively, "sideboard" on one or more lateral sides of the introducer 100. At any of these various locations, the curved instrument will exert, due to the bias or spring force it causes as it bends, a force on the outer sheath 134 of the main channel 122 and/or the guide channel 118.

Thus, as illustrated in FIG. 4, the guide channel 118 of the present invention is provided with a guide platform or other type of guide rail 148 in order to actually guide the instrument 112 in its path along the guide channel 118. Thus, even though the instrument 112 may be bending and flexing, it will tend to be retained in its path along the guide platform 148, which acts as a rail or track for the instrument to follow. As illustrated in FIG. 4, in one preferred embodiment the guide rail 148 comprises the slit 136 in the split sheath 134 of the main endoscopic channel 122. The longitudinal guiding capabilities of this slit 136 are also illustrated in FIG. 4. However, other guide platform configurations are possible, such as a D-shaped main tube (not shown) which has a flattened area for instrument travel thereupon. This flattened area could also contain recesses or slots to further facilitate directed insertion of the instrument. In any particular guide channel and guide rail configuration, the guide channel membrane 140 is able to assume a number of storage or set positions, as described above.

Thus, the guide platform 148 may be flattened or provided with lateral walls in order to provide sure guidance for the curved instrument. Therefore, in accordance with an important advantage of the present invention, the surgical access device 100 can be used to guide an instrument 112 along a specified path with respect to the main channel 122 so that it achieves accurate placement with respect to a specific location at the distal end of the access device 100.

An alternate embodiment (not shown) of the guide channel of the present invention is characterized by a perforated or serrated guide channel membrane. In this embodiment, the guide channel is provided with a reduced diameter in the region of its distal tip. However, in this region or at other regions along the longitudinal length of the guide channel, the membrane is perforated or serrated in order to facilitate its release as a secondary instrument is advanced. Furthermore, the perforations or slits can be such that the guide channel opens up completely in order to allow instrument access to the lateral regions of the access device. Such perforated or serrated guide channels also provide other guide channel storage options, as well as other advantages which will be apparent to one of ordinary skill.

Distal Portion

In one embodiment of a distal tip 156 of the access device, shown in FIG. 5, a tapered distal profile of the access device 100 facilitates the insertion process; however, the extreme distal edge is rounded or blunt in order to avoid damage to the tissue. Holes 158 shown in the distal tip 156 are necessary to provide aspiration and avoid choking of irrigation media. In this embodiment, the guide channel 118 at the distal tip 156, which is shown folded back on the outer surface 120 of the split sheath 134, can be securely sealed to the body of the introducer 100 by a heat seal process. Thus, the guide channel 118 is sealed and is impervious against contamination or distortion as the access device 100 is introduced into the body. Alternatively, the distal end of the introducer can be shaped so as to have an annular mound at the distal tip of the guide channel and just proximal of the distal tip of the access device (not shown). Likewise, this mound can serve to protect the distal end of the guide channel against contamination or damage as the access device is introduced into the body and navigated through its various anatomy.

One particularly preferred embodiment of a distal tip 200 of an introducer for biopsies is shown in FIGS. 8–10. As shown, an open-loop device 202 is formed on a curved distal tip of a main channel 204. Using an endoscope 206 positioned in the main channel 204, the device 202 may be manipulated by the physician to collect a tissue specimen. A hole 208 formed in the distal tip 200 provides a greater viewing field for the endoscope 206 of the tissue sample area. A guide channel 210 is preferably provided in an outboard configuration, and the device 202 has a curved length preferably extending past an inboard side 212 of the introducer. Alternatively, the guide channel 210 may be formed on the inboard side (see FIG. 8 in phantom). Further, the length of the curved device 202 may be shorter so as not to extend past the inboard side 212 of the introducer. During endoscopic surgery, as discussed in greater detail below with regard to the method of use of the present device, an aspiration tube 214 may be provided in the guide channel 210 as shown in FIGS. 8 and 10 for removal of a tissue specimen comprising either separate cells or a tissue section.

It should also be noted, with regard to the introducer of FIGS. 8–10, that although the distal tip is shown without particular shaping for sealing the guide channel and such as described heretofore, it is understood that other shapes for sealing at the distal tip of the introducer may be readily incorporated.

Proximal Housing Portion

Figure 6:
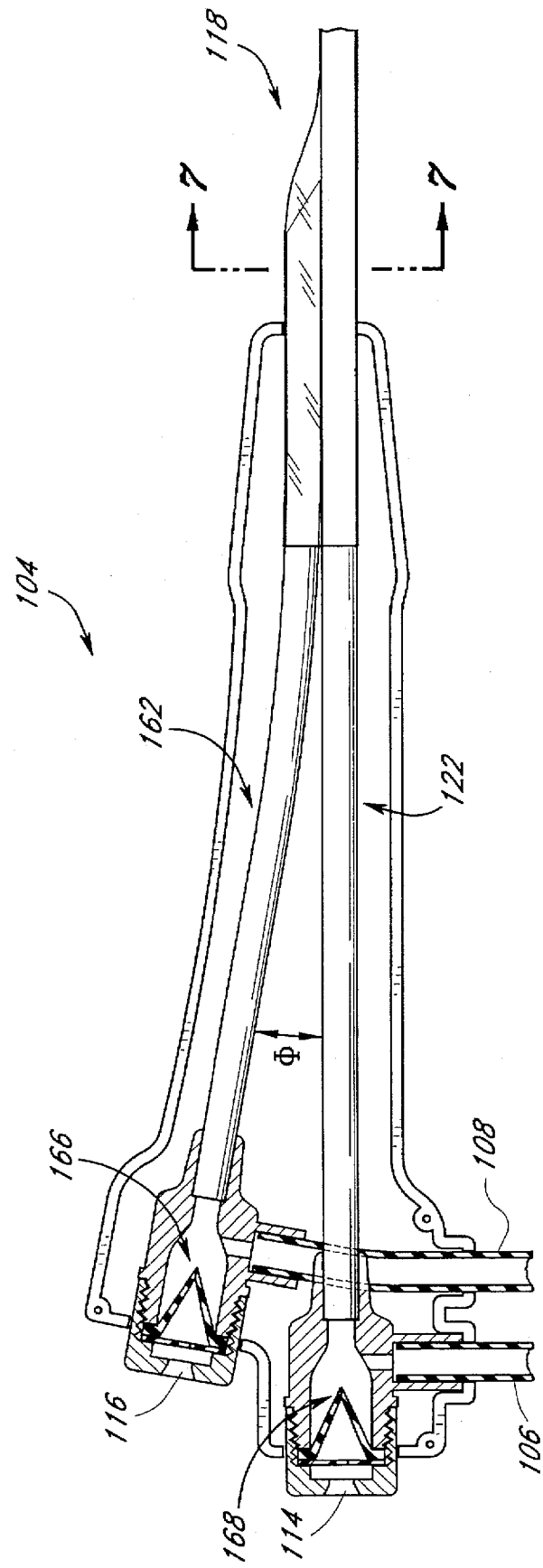
FIG. 6 is a longitudinal cross-sectional view taken through the proximal housing of the present access device in order to illustrate the merge channel leading into the guide channel of the present invention.

As explained above in connection with FIG. 1, the proximal housing portion 104 of the present invention surrounds the main endoscopic channel 122 and a merge channel 162 positioned above it in FIG. 6. The merge channel 162 allows an endoscope or secondary instrument 112 to be inserted through it for deployment through the guide channel 118, shown in its pre-deployment position in FIG. 6. The merge channel 162 also allows a proximal handle 163 of the instrument 112 to be offset or displaced with respect to any endoscope 110 or instrument inserted in the main channel 122 in order to facilitate use of the access device 100 by the physician.

Figure 7:
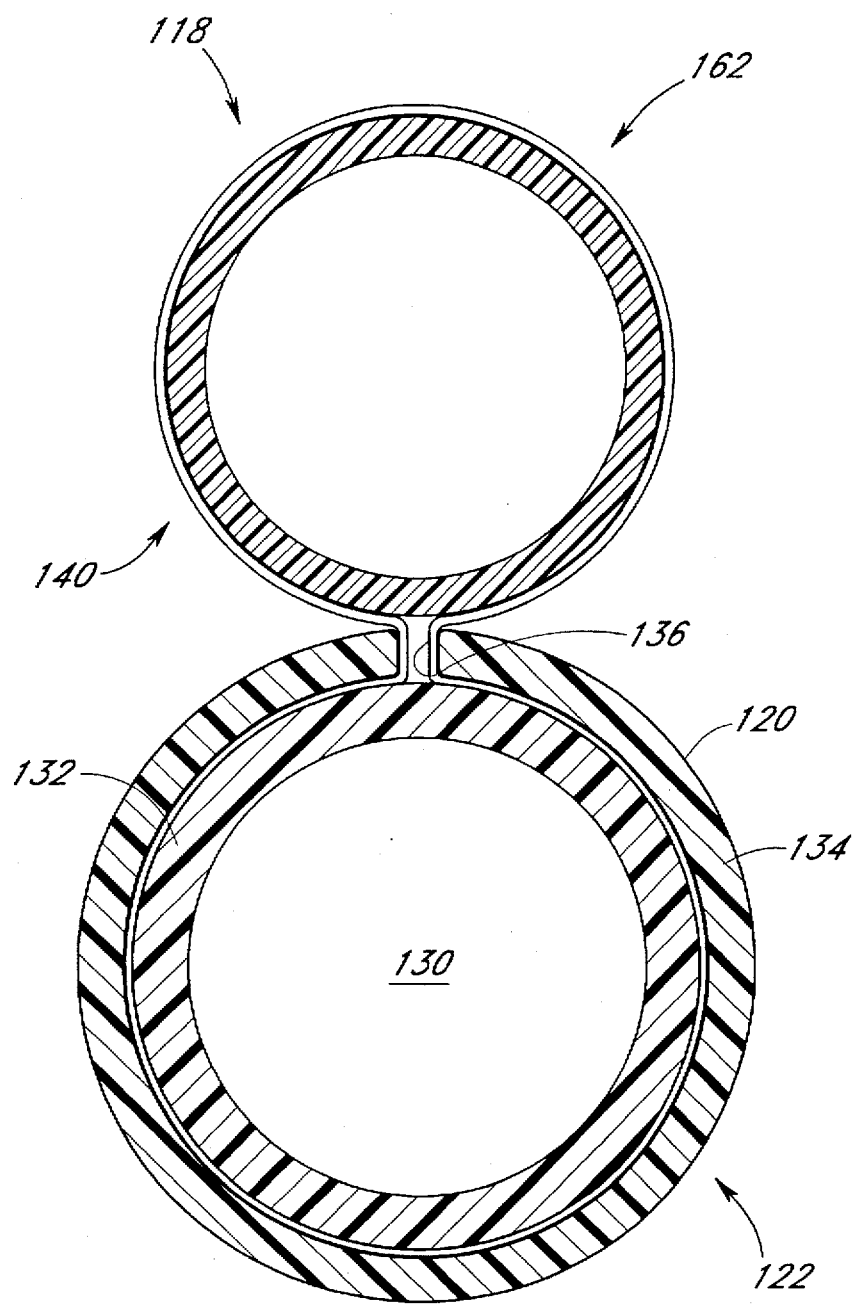
FIG. 7 is a cross-sectional view taken along lines 7—7 of FIG. 6 illustrating the merge channel and main channel distal the proximal housing of the present access device.

With reference to FIGS. 6 and 7, the proximal housing portion 104 of the surgical access device 100 of the present invention can be described. FIG. 6 is a partial cross-sectional view of the side of the access device 100, while FIG. 7 is a cross-sectional view taken along lines 7—7 of FIG. 6 in which is illustrated the piggyback arrangement of the main or endoscopic channel 122 and the merge channel 162 of the housing 104.

With reference to FIG. 6, it will be seen that the merge channel 162 converges upon the main channel 122 at a shallow angle $\phi$, gradually becoming asymptotic or tangential thereto. The merge angle $\phi$ should be sufficient to allow a slight bending or curvature in the instrument 112 being inserted through the merge channel 162 and into the guide channel 122; preferably, an angle $\phi$ of about 4°–300° is satisfactory, with about 11° preferred.

At the extreme proximal end of the housing portion 104, there is shown an inflow conduit 106 associated with the main channel 122 and an outflow conduit 108 associated with the merge channel 162. Depending upon the procedure being performed, the inflow conduit 106 may be utilized to pass distension or irrigation media down the main channel 122 to the distal end of the access device 100. Having the distension media run through the main tube 132 and around the endoscope 110 also allows for fluid to travel across the optics at the distal end of the endoscope 110, keeping this area free of blood and debris and thereby improving visualization. The outflow channel 108 can be used to provide aspiration or other evacuation of fluids. Also, of course, the function of these conduits 106, 108 can be reversed or utilized in connection with multiple channels, as the case necessitates. In each case, duckbill valves 166, 168 are preferably formed at the main or endoscopic port 114 and at the instrument port 116 in order to prevent the escape of fluids prior to insertion of the instruments into these respective channels 122, 162. Likewise, O-ring structures or washer elements prevent the escape of fluids around an endoscope 110 or instrument 112 when inserted through the ports 114, 116. However, it will be understood that other types of valving and conduit mechanisms can be utilized in connection with the present access device 100.

The cross-sectional view of FIG. 7 also illustrates the association of the guide channel membrane 140 with respect to the merge channel 162. That is, the membrane 140 is shown extending through the slit or neck 136 in the split sheath 134 and completely around the merge channel 162. Advantageously, the guide channel membrane material can be heat formed onto both channels 122, 162 in order to provide some rigidity and strength to the proximal housing portion 104 of the access device 100. In fact, the membrane 140 can be extended proximally any desired distance, as indicated in FIG. 6.

In addition to a aspiration tube which may be inserted through the guide channel of the present device, surgical instruments comprising cutting or scraping elements, such as biopsy forceps, a curette or the like, may also be used with the introducer. The self-adjusting nature of the guide channel, in its various embodiments described herein, advantageously accommodating any diameter of instrument inserted through the merge channel and into the guide channel.

Method of Performing Biopsy or Other Surgical Cutting Procedures

Preferably, in an endoscopic surgery such as hysteroscopy where a biopsy is either planned or optionally to be performed, the physician inserts the introducer through the port into the patient and supplies distension media to inflate the uterine cavity for visibility therein. An aspiration tube is optionally inserted into the guide channel for outflow, which provides circulating means to clear debris, mucus or blood from the field of vision. Thus, inflow and outflow tubes for distension/irrigation may be provided on the introducer to facilitate circulation. An endoscope inserted through the main channel of the introducer is used to view the area around the distal tip of the introducer. Once an area is found from which a sample is desired, an appropriate instrument, such as a biopsy instrument or curette, is optionally inserted through the guide channel, expanding the membrane 140 as it advances to the distal tip. Alternatively, the instrument may be inserted through the main channel concurrently with the endoscope. An electrical surgical generator (not shown) may be provided for supplying electrical cutting or coagulating means at the distal end of the instrument, which may be a loop or coagulation electrode, for example. As can be discerned from the foregoing operating steps, the introducer's main and guide channels may each be used with a plurality of instruments for performing several surgical functions during the same surgery.

In a preferred embodiment of an open-loop device 202 being provided on the main channel of the introducer, the endoscope is inserted into the main channel and its field of vision is enhanced by the hole 208 in the distal tip of the main channel. An aspiration tube inserted through the guide channel removes blood at the viewing area or may be used to remove the specimen. An inboard or outboard configuration of the guide channel may be utilized. Alternatively, the endoscope and aspiration tube may be switched, so that the endoscope is in an inboard guide channel, for example.

For other electrosurgical instruments to be utilized with the present device, a power source is connected at a distal end of the introducer for supplying the instrument. Such instruments may be used, for example, to cut or for coagulation at the area being operated upon. A video camera for easier viewing through the endoscope may also be used by the physician during the endoscopic procedure.

Thus, the present invention generally comprises an apparatus and method of obtaining a tissue specimen from a patient during endoscopic surgery, a surgical access device being provided which has a substantially rigid main channel and an expandable guide channel. The guide channel initially has a pre-deployment, or pre-insertion, position such that a cross-section of an inserted portion of the device is substantially the same as a cross-section of the main channel, the device having a curved distal end. In the method of the present invention, a port is established in the patient for entry of the device, as either an orifice or an incision made by the physician, and the device is inserted into the port, with the guide channel in its first position to facilitate entry into the patient's body, thereby minimizing patient discomfort.

An endoscope is inserted through one of the channels for viewing therethrough, and the device is positioned according to visual information obtained from the endoscope in order to locate a desired tissue specimen. The tissue specimen is removed from the patient, and the device is removed from the port in the patient. The various insertions and removals of secondary instruments, if any, during the surgical procedure are facilitated by a merge channel at a proximal end of the device and the noncompliant nature of the material forming the guide channel, the guide channel being self-adjusting to a diameter of the instrument inserted therethrough.

In conclusion, the surgical access device of the present invention and the method of its use in biopsy and other surgical cutting procedures represents a marked advancement in the art. Thus, it should be understood that the scope of the present invention is not to be limited by the illustrations or foregoing description thereof, but rather by the appended claims, and certain variations and modifications of this invention will suggest themselves to one of ordinary skill in the art.

What is claimed is:

1. A surgical access device for obtaining tissue during endoscopic surgery, said surgical device having a proximal end, a distal end and an elongate body extending therebetween, said surgical access device also having an outer surface defining at any particular location along its longitudinal axis, a cross-sectional profile, said surgical access device comprising:

a first channel providing a first lumen for the insertion of an instrument, endoscope or other visualization device;

an open-loop member at a distal end of said first channel, said open-loop member having a transverse aperture formed therethrough, said aperture facing laterally outwardly from the longitudinal axis of said surgical access device; and at least one secondary channel providing a secondary lumen for the insertion of an instrument, endoscope or other visualization device, said secondary channel being mounted on said surgical access device so as to be positioned along said outer surface thereof, said secondary channel being constructed from a thin pleated membrane which, prior to dilation of said secondary channel, is self-retained along the outer surface of said first channel.

2. The surgical access device of claim 1, wherein said distal end of said surgical access device is curved and said secondary channel extends along a generally convex side of said first channel.

3. The surgical access device of claim 2, wherein said secondary channel is in fluid communication with said aperture formed through said open-loop member.

4. The surgical access device of claim 1, wherein said secondary channel extends along a generally concave side of said first channel.

5. The surgical access device of claim 1, wherein said secondary channel is formed at least in part by a substantially noncompliant material.

6. The surgical access device of claim 1, wherein said distal end of said surgical access device is curved, forming an angle from the longitudinal axis of said surgical access device of between approximately 5°–30°.

7. A method of obtaining a tissue specimen from a patient during endoscopic surgery, comprising:

providing an access device having a proximal end, distal end and an elongate body extending therebetween, the access device comprising a first channel providing a first lumen for the insertion of an instrument, endoscope or other visualization device, the first lumen having a substantially fixed cross-sectional area; at least one secondary channel providing a secondary lumen for the insertion of an instrument, endoscope or other visualization device, said secondary channel being mounted on the access device so as to be positioned along an outer surface thereof, said secondary channel being constructed at least in part by a flexible wall, the secondary lumen having an internal cross-sectional area that is movable from a first, reduced area to a second, enlarged area; and a transverse aperture formed through a wall beyond the distal end of the first channel;

percutaneously advancing the access device into the patient while the secondary lumen is in the first, reduced cross-sectional area configuration in order to minimize patient discomfort;

enlarging the diameter of the secondary lumen from the first, reduced cross-sectional area to the second, enlarged cross-sectional area to provide percutaneous access to said tissue specimen by way of the secondary lumen; and removing said tissue specimen from the patient.

8. The method of claim 7, further comprising:

introducing an endoscope into the first lumen of the access device either before or after the step of percutaneously advancing the access device into the patient; and positioning the access device using visual information obtained from the endoscope to locate said tissue specimen.

9. The method of claim 8, further comprising supplying distension media through the access device.

10. The method of claim 8, wherein the step of percutaneously advancing the access device into the patient is preceded by the additional steps of identifying an access site on the patient, and making an incision at the access site for receiving the access device.

11. The method of claim 10, further comprising withdrawing the endoscope and the access device from the patient.

12. The method of claim 7, wherein the removing said tissue step comprises inserting a biopsy instrument through the secondary lumen for retrieval of said tissue specimen.

13. The method of claim 7, wherein the removing said tissue step comprises manipulating the open-loop member to excise said tissue specimen.

14. The method of claim 13, wherein the removing said tissue step further comprises inserting an aspiration tube in the secondary lumen so that the aspiration tube is in fluid communication with the aperture formed through the open-loop member.

15. A surgical access device for obtaining tissue during endoscopic surgery, said surgical access device having a proximal end, a distal end and an elongate body extending therebetween, said surgical access device also having an outer surface defining at any particular location along its longitudinal axis, a cross-sectional profile, said surgical access device comprising:

a first channel providing a first lumen for the insertion of an instrument, endoscope or other visualization device;

an open-loop member at a distal end of said first channel, said open-loop member having an aperture formed therethrough; and at least one secondary channel providing a secondary lumen for the insertion of an instrument, endoscope or other visualization device, said secondary channel being mounted on said surgical access device so as to be positioned along said outer surface thereof, said secondary channel being constructed from a thin pleated membrane which, prior to dilation of said secondary channel, so closely conforms to said outer surface so as to only negligibly increase the size of said profile of said surgical access device;

wherein said distal end of said surgical access device is curved and said secondary channel extends along a generally convex side of said first channel, and said secondary channel is in fluid communication with said aperture formed through said open-loop member.

16. The surgical access device of claim 15, wherein said secondary channel is formed at least in part by a substantially noncompliant material.

17. The surgical access device of claim 15, wherein the curved distal end of said surgical access device forms an angle from the longitudinal axis of said surgical access device of between approximately 5°–30°.

18. A method of obtaining a tissue specimen from a patient during endoscopic surgery, comprising:

providing an access device having a proximal end, distal end and an elongate body extending therebetween, the access device comprising a first channel providing a first lumen for the insertion of an instrument, endoscope or other visualization device, the first lumen having a substantially fixed cross-sectional area, the access device also comprising at least one secondary channel providing a secondary lumen for the insertion of an instrument, endoscope or other visualization device, said secondary channel being mounted on the access device so as to be positioned along an outer surface thereof, said secondary channel being constructed at least in part by a substantially inelastic flexible wall, the secondary lumen having an internal cross-sectional area that is movable from a first, reduced area to a second, enlarged area;

percutaneously advancing the access device into the patient while the secondary lumen is in the first, reduced cross-sectional area configuration in order to minimize patient discomfort;

enlarging the diameter of the secondary lumen from the first, reduced cross-sectional area to the second, enlarged cross-sectional area to provide percutaneous access to said tissue specimen by way of the secondary lumen; and removing said tissue specimen from the patient;

wherein the access device further comprises an open-loop member at a distal end of said first channel, said open-loop member having an aperture formed therethrough, wherein the removing said tissue step comprises manipulating the open-loop member to excise said tissue specimen.

19. The method of claim 18, further comprising:

introducing an endoscope into the first lumen of the access device either before or after the step of percutaneously advancing the access device into the patient; and positioning the access device using visual information obtained from the endoscope to locate said tissue specimen.

20. The method of claim 19, farther comprising supplying distension media through the access device.

21. The method of claim 19, wherein the step of percutaneously advancing the access device into the patient is preceded by the additional steps of identifying an access site on the patient, and making an incision at the access site for receiving the access device.

22. The method of claim 21, farther comprising withdrawing the endoscope and the access device from the patient.

23. The method of claim 18, wherein the removing said tissue step comprises inserting a biopsy instrument through the secondary lumen for retrieval of said tissue specimen.

24. The method of claim 18, wherein the removing said tissue step further comprises inserting an aspiration tube in the secondary lumen so that the aspiration tube is in fluid communication with the aperture formed through the open-loop member.

25. A surgical access device for obtaining tissue during endoscopic surgery, said surgical access device having an outer surface defining at any particular location along its longitudinal axis, a cross-sectional profile, said device comprising:

a tubular wall providing a first lumen for the insertion of an instrument, endoscope or other visualization device, said tubular wall having a proximal end, a distal end and a distal extension on the distal end;

at least one collapsible secondary wall providing a secondary lumen for the insertion of an instrument, endoscope or other visualization device, said secondary wall mounted on an outer surface of the tubular wall; and a traverse aperture formed through the distal extension on the tubular wall.

* * * * *

UNITED STATES PATENT AND TRADEMARK OFFICE
CERTIFICATE OF CORRECTION

PATENT NO. : 5,749,889
DATED : May 12, 1998
INVENTOR(S) : Bacich, et al.

It is certified that error appears in the above-identified patent and that said Letters Patent is hereby corrected as shown below:

In Claim 20, column 22, line 55, change "farther comprising" to -- further comprising --.

In Claim 22, column 22, line 62, change "farther comprising" to -- further comprising --.

Signed and Sealed this

Eighth Day of February, 2000

*Attest:*

Q. TODD DICKINSON

*Attesting Officer*     *Commissioner of Patents and Trademarks*